United States Patent

Brearley et al.

Patent Number: 5,532,487
Date of Patent: Jul. 2, 1996

[54] NEAR-INFRARED MEASUREMENT AND CONTROL OF POLYAMIDE PROCESSES

[75] Inventors: Ann M. Brearley, West Chester, Pa.; Harvey S. Gold, Newark, Del.

[73] Assignee: E. I. Du Pont de Nemours and Company, Wilmington, Del.

[21] Appl. No.: 344,426

[22] Filed: Nov. 23, 1994

[51] Int. Cl.[6] .......................... G01J 5/02; G01N 30/28; G01N 33/00; G01N 23/00
[52] U.S. Cl. .............................. 250/339.12; 250/339.07; 250/339.08; 250/339.09; 250/340; 526/59; 526/60; 526/61; 526/310; 526/317.1; 526/321; 526/332; 528/332; 528/335; 528/207
[58] Field of Search .............. 250/339.07, 339.09, 250/339.12, 339.08, 340; 528/335, 339, 340, 347, 310, 317.1, 321, 332, 207; 526/59, 60, 61

[56] References Cited

U.S. PATENT DOCUMENTS

| | | | |
|---|---|---|---|
| 3,509,106 | 4/1970 | Lotz et al. | 526/59 |
| 3,658,534 | 4/1972 | Ishitani et al. | 96/48 |
| 3,796,692 | 3/1974 | Foltz et al. | 526/59 |
| 3,985,714 | 10/1976 | Kiddler | 526/59 |
| 4,742,131 | 5/1988 | Asanuma et al. | 526/61 |
| 5,015,856 | 5/1991 | Gold | 250/339 |
| 5,121,337 | 6/1992 | Brown | 364/498 |
| 5,151,474 | 9/1992 | Lange et al. | 526/60 |
| 5,155,184 | 10/1992 | Laurent et al. | 526/59 |
| 5,339,255 | 8/1994 | Suzuki et al. | 364/500 |
| 5,349,189 | 9/1994 | Maggard | 250/339.12 |
| 5,360,972 | 11/1994 | DiFoggio et al. | 250/339.12 |

FOREIGN PATENT DOCUMENTS

| | | | |
|---|---|---|---|
| 53055385 | 5/1978 | Japan | 526/59 |
| WO91/15762 | 10/1991 | WIPO | |

OTHER PUBLICATIONS

Vol. 17, "Encyclopedia of Industrial Chemical Analysis", John Wiley & Sons (1973).

Primary Examiner—Constantine Hannaher
Assistant Examiner—Virgil O. Tyler

[57] ABSTRACT

This invention relates to a method for the measurement and control of polyamides and polyamide precursor mixtures by means of near-infrared spectroscopy.

13 Claims, 3 Drawing Sheets

NEAR-INFRARED MEASUREMENT AND CONTROL OF POLYAMIDE PROCESSES

FIELD OF THE INVENTION

This invention concerns near-infrared spectroscopy and its use as an analytical method to measure a variety of characteristics and control various steps in processes for the manufacture of polyamide, especially nylon 6,6.

TECHNICAL BACKGROUND

Analysis of polyamides has been an area of technical study since the invention of this important class of compounds. A multitude of analytical methods have been developed to study various characteristics in the product polyamides and have also been used at various stages of polyamide manufacturing processes. See, for example, Volume 17 of the "Encyclopedia of Industrial Chemical Analysis" published by John Wiley & Sons (1973). These earlier methods are applicable to the analysis of nylon polyamide product or to various stages of nylon polyamide processes. When applied to process-related measurements, the methods suffer from the fact that a discrete sample of the in process material must be taken and analyzed. This sampling and analysis can be a cause of inaccuracy and irreproducibility because of the nature of the nylon polymerization reaction, i.e., the reaction continues at a rate determined by the temperature of the material and the atmosphere surrounding the material. The invention of the present application, when applied to process related materials, avoids these problems because the analysis requires the taking of no samples, e.g., from a continuous process. This aspect of the invention at hand is an in-line analytical method.

U.S. Pat. No. 5,155,184 discloses a process for the manufacture of a polymer, the process being controlled by periodically sampling the polymer produced and analyzing the sample by near-infrared spectrophotometry. The polymer produced is a polyolefin, more specifically, polyethylene.

U.S. Pat. No. 5,339,255 describes a process for measuring an infrared spectral absorption of a reaction intermediate product of polycondensation reaction and mentions applicability to polyamide.

SUMMARY OF THE INVENTION

This invention provides a method for the measurement and control of various characteristics comprising concentration of carboxylic acid ends, concentration of amine ends, ends balance, relative viscosity, dyeability, concentration of finish on yarn, and additive concentration of a dimonomeric polyamide or copolyamide in the melt phase or solid state or of a polyamide precursor mixture at selected points in a polyamide polymerization process using near-infrared spectroscopy.

This invention provides a method for measuring and controlling at least one characteristic of a dimonomeric polyamide, copolyamide, or polyamide precursor mixture in a polymerization process stream, comprising the steps of:

(a) creating a predictive model for the value of the characteristic;

(b) acquiring spectra by measuring the near-infrared absorbance of the polyamide, copolyamide or polyamide precursor mixture inn-line at at least one selected point in the polymerization process stream at wavelengths within the range of about 600 nm to about 2500 nm;

(c) applying spectral pretreatment to the measurements of step (b) to obtain a pretreated spectrum;

(d) applying the predictive model to the pretreated spectrum to calculate a predicted value of the characteristic;

(e) comparing the predicted value of the characteristic to a preselected desired value of the characteristic; and (f) controlling the characteristic by making an adjustment to at least one process variable of the polymerization process stream.

The present invention further provides a method for measuring and controlling at least one characteristic of a solid phase dimonomeric polyamide or copolyamide, comprising the steps of:

(a) creating a predictive model for the value of the characteristic;

(b) acquiring spectra by measuring the near-infrared absorbance of the polyamide or copolyamide at-line within the range of about 600 nm to about 2500 nm;

(c) applying spectral pretreatment to the measurements of step (b) to obtain a pretreated spectrum;

(d) applying the predictive model to the spectrum to calculate a predicted value of the characteristic;

(e) comparing the predicted value of the characteristic to a preselected desired value of the characteristic; and (f) controlling the characteristic by making an adjustment to at least one process variable of the polymerization process stream.

DETAILED DESCRIPTION OF THE INVENTION

Figure 1A:
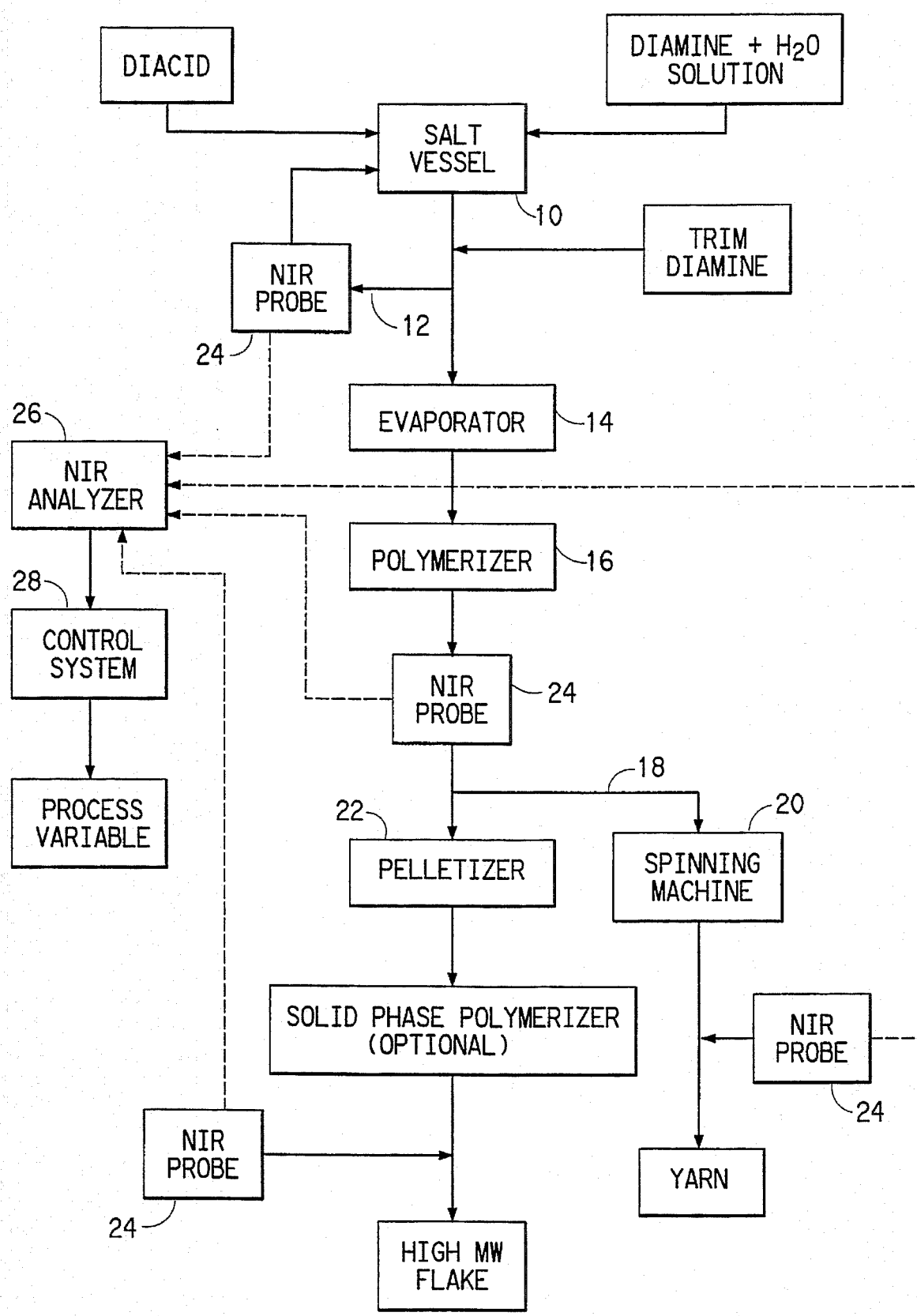
FIG. 1A is a flowsheet of an aqueous process for manufacturing (either batch or continuous) dimonomeric polyamide or copolyamide using a near-infrared analyzer for measuring and controlling the process.

This invention provides improved measurement and process control of various characteristics of dimonomeric polyamides and copolyamides in both the melt phase and solid state, as well as, various characteristics of polyamide precursor mixtures. Many characteristics are affected by even subtle changes in process variables, so that, contrary to intuitive expectations, it is impossible to accurately predict in advance the value of a particular characteristic of a polyamide or polyamide precursor mixture from its content or from the nominal process conditions. It is, therefore, necessary to be able to ascertain on a regular basis whether or not production runs are producing products which satisfy particular standards.

It is therefore desirable to have available an instrumental process for quickly and reliably determining the value of various characteristics so that any departures from the standards can be readily recognized, and any necessary corrective action can be taken promptly.

To produce a product with time-wise uniformity suitable for commercial end uses, it is necessary to monitor and control various characteristics of the polyamide precursor mixture and/or the product itself. For example, it is necessary to monitor and control the difference between the concentration of the carboxylic acid functional end groups and the concentration of amine functional end groups in the resulting dimonomeric polyamide or copolyamide by an appropriate control system. This requirement is especially stringent for product that will eventually be formed into fibers that will be treated with dyes that attach themselves to one or the other of the two functional groups.

To achieve control of precursor mixtures, a measurement can be made of some characteristic in the polymer leaving the final stage of the reactor or of the mixture at the exit of the equipment wherein the precursor mixture is made up which characteristic is sufficiently sensitive to the concentration difference. The method must be accurate to within about plus or minus 0.5 units in the difference in acid and amine concentrations in milliequivalents/kg of precursor or polymer resulting from the precursor mixture. An analytical method with tiffs approximate accuracy must be rapid enough to give answers in real-time, i.e., in a timely enough fashion to effect process control. In general, manual titrimetric methods, though sufficiently accurate, are not rapid enough to give meaningful process control.

The present invention is a rapid, reliable, in-line method, or for solid phase polyamide inn-line or at-line method, which methods apply near-infrared (NIR) spectroscopy to the analysis of polyamides, for example, nylon precursors and nylon polymer, and covers applications that span use for salt balance in nylon salt, i.e., diacid plus diamine salt, to determining relative viscosity (RV) and endgroup balance for standard polymer products and RV for high (100–300) RV polymer. By relative viscosity is meant the ratio of solution and solvent viscosities measured in a capillary viscometer at 25° C. The solvent is formic acid comprising 10% by weight water. The solution is 8.4% by weight polyamide dissolved in solvent. Other characteristics for measurement and control comprise concentration or number of carboxylic acid ends or amine ends, ends balance, dyeability, concentration of finish on yarn and additive concentration. NIR can quickly and accurately predict these characteristics under any process conditions and detect departures from the standards, thus making it possible to immediately adjust process variables to attain the desired characteristic value.

Dimonomeric polyamides useful in the present invention comprise polyamides prepared by the condensation polymerization of two monomers, a diacid and a diamine, for example, nylon 6,6 which is a polyamide prepared from adipic acid (1,6-hexanedioic acid) and hexamethylene diamine.

The diacid component can be selected from aliphatic, alicyclic or aromatic diacids. The diacid can be used in solid form or it can be used in melt form by itself or as a melt or dispersion in combination with other diacids or as an acid-rich feed with diamine at a temperature that avoids excessive degradation of the diacid or dissolved in an appropriate solvent in an aqueous salt. Specific examples of such acids include glutaric acid, adipic acid, suberic acid, sebacic acid, dodecanedioic acid, 1,2- or 1,3-cyclohexane dicarboxylic acid, 1,2- or 1,3-phenylene diacetic acid, 1,2- or 1,3-cyclohexane diacetic acid, isophthalic acid, terephthalic acid, 4-4'oxybis (benzoic acid), 4,4'-benzophenone dicarboxylic acid, 2,6-naphthalene dicarboxylic acid, and p-t-butyl isophthalic acid. The preferred dicarboxylic acid is adipic acid.

The diamine component can be selected from the group consisting of aliphatic, alicyclic or aromatic diamines. Specific examples of such diamines include hexamethylene diamine, 2-methylpentamethylenediamine, 2-methyl hexamethylene diamine, 3-methyl hexamethylene diamine, 2,5-dimethyl hexamethylene diamine, 2,2-dimethylpentamethylene diamine, 5-methylnonane diamine, dodecamethylene diamine, 2,2,4- and 2,4,4-trimethyl hexamethylene diamines, 2,2,7,7-tetra-methyl octamethylene diamine, meta-xylylene diamine, para-xylylene diamine, diaminodicyclohexyl methane and $C_2$–$C_{16}$ aliphatic diamines which may be substituted with one or more alkyl groups. The preferred diamine is hexamethylene diamine.

An optional third starting material, having a carboxylic acid functional group and an amino functional group or a functional precursor to such a compound, may be selected from 6-aminohexanoic acid, caprolactam, 5-aminopentanoic acid, 7-aminoheptanoic acid and the like.

In general, at least one characteristic of the dimonomeric polyamide precursor mixture and/or resultant polyamide or copolyamide in a melt phase can be analyzed and predicted at various in-line selected points in the polymerization process stream or for solid phase polyamide in-line or at-line by the application of near-infrared spectroscopy. Then based on the analysis, subsequent control action adjustments to process variables comprising flow rate of diacid, diamine or additives; temperature; and pressure can be made.

The method requires establishing a correlation between the characteristic of interest using samples of a calibration set and their near-infrared spectra, creating from that correlation a predictive model in the form of an equation, verifying the accuracy of the predictive model on samples of a validation set, applying the predictive model to the determination of the composition of unknown samples and making the appropriate control adjustments.

The dimonomeric polyamide or copolyamide of the present invention can be prepared in an aqueous process. As shown in FIG. 1A, diamine, diacid and water are combined to form an aqueous salt solution in salt vessel 10. Trim diamine can be added to the salt solution via recirculating loop 12. Polycondensation of the salt can take place in batch or continuous mode. Because the batch process requires careful handling to avoid nonuniformity in quality, not only from batch to batch but even in the same batch, the continuous process is preferred. The water is evaporated from the heated aqueous salt solution, and the salt passes to polymerizer 16 where condensation occurs resulting in the formation of polyamide. The product is in a molten state. This molten polymer can then be transferred via melt transfer line 18 to spinning machine 20 for subsequent processing into, for example, yarn or the molten polymer can be transferred from polymerizer 16 to pelletizer 22, and optionally to further processing into high molecular weight flake.

NIR probe 24 can be located at various selected in-line points in the aqueous polymerization process and is shown in FIG. 1A in recirculating loop 12 to measure characteristics in the aqueous salt solution, between polymerizer 16 and pelletizer 22 to measure characteristics of the polymer melt. NIR probe 24 can also be located at-line, for example, after spinning machine 20 to measure fiber characteristics, and after the pelletizer 22 in-line or at-line to measure characteristics of solid phase polyamide. The at-line embodiment after pelletizer 22 is shown in FIG. 1A. These probes are linked to NIR analyzer 26 which is in turn linked to control system 28 which makes appropriate adjustments to process variables as needed.

NIR based analysis can be used to determine, for example at a nylon 6,6 salt stage, both the relative amounts of adipic acid and hexamethylene diamine (i.e., balance) and the total amounts of each (i.e., concentration). These are conveniently expressed as ends difference in milliequivalents per kilogram (meq/kg) and salt concentration (in weight %). Ends difference can also be expressed as salt pH. If the preparation of the salt is carried out in a continuous fashion, the analysis and control can also be carried out essentially continuously. Depending on the values of ends balance and salt concentration obtained, and the desired values of these characteristics, changes in the reactant amounts and ratios can be made.

In a preferred process wherein the dimonomeric polyamide or copolyamide is prepared in a continuous, non-aqueous fashion, the feed stream comprises a flowable molten diacid or a flowable molten diacid rich mixture comprising the selected diacid and diamine. In the case where the process is used for the preparation of nylon 6,6, the feed stream for the process comprises flowable molten adipic acid or a flowable molten adipic acid-rich mixture comprising adipic acid and hexamethylene diamine.

Figure 1B:
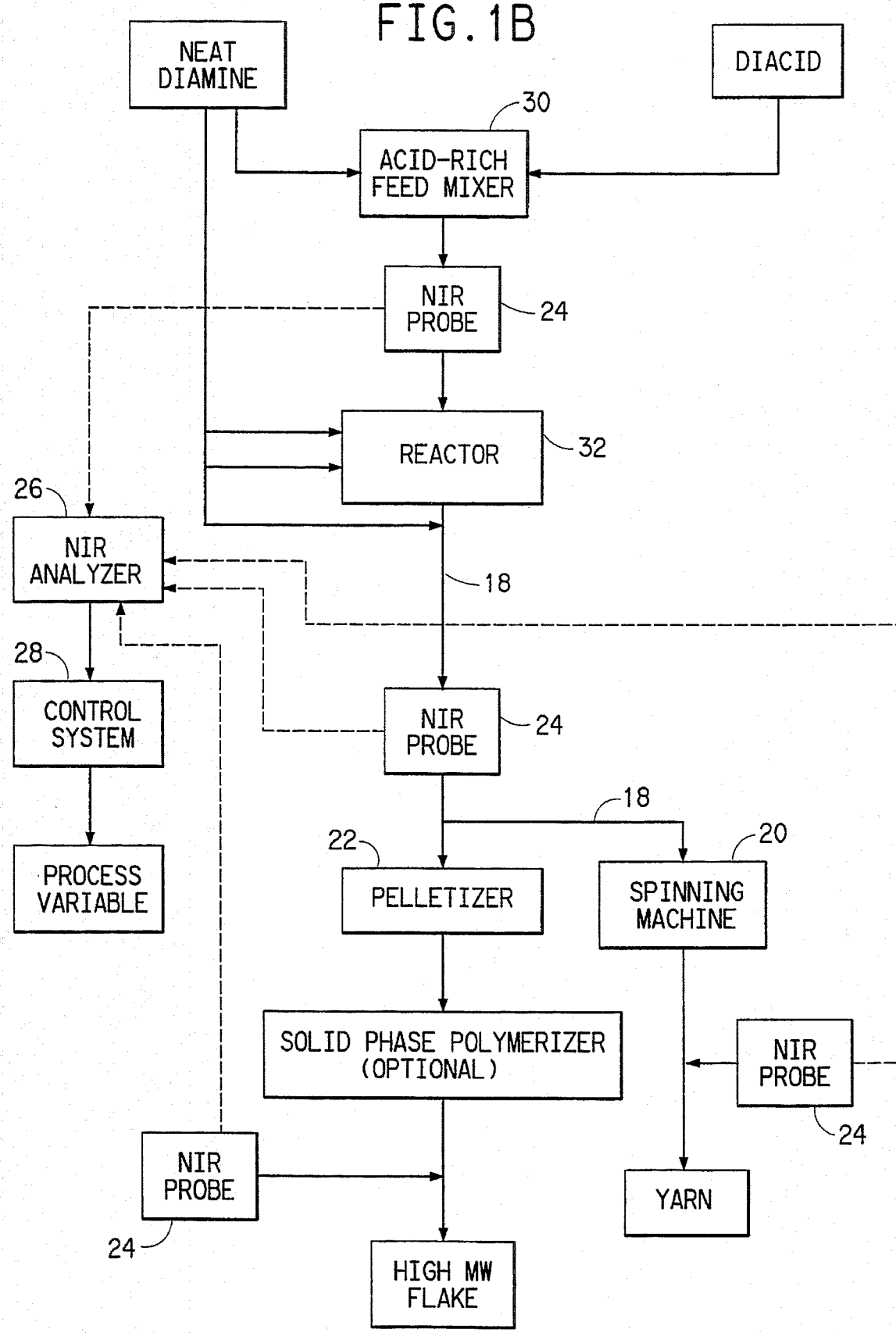
FIG. 1B is a flowsheet of a preferred non-aqueous, continuous process for the manufacture of dimonomeric polyamide or copolyamide using a near-infrared analyzer for measuring and controlling the process.

As shown in FIG. 1B, diacid or diacid mixed with diamine feed is prepared in mixer 30 and then fed, as a molten liquid, into the top of multi-stage reactor 32 at essentially atmospheric pressure.

In a most preferred mode, the exit stream from the acid-rich feed mixer 30 to the first stage of reactor 32 is continuously monitored by near-infrared spectrophotometry via NIR probe 24 connected to NIR analyzer 26. NIR analysis at this selected in-line point can predict the composition, expressed as weight % adipic acid. Based on this analysis, control adjustments can be made in process variables, such as the ratio of reactant feeds. For nylon 6,6 this process variable could be the ratio of the hexamethylenediamine feed rate to the adipic acid feed rate.

The non-aqueous polymerization reaction is conducted in reactor 32, an apparatus equipped with internals, perforated plates, coils and agitators, to cause effective contact of counter-currently flowing diamine or diamine-rich vapor with the molten acid or acid-rich feed so as to achieve rapid, efficient scrubbing of the diamine from the countercurrently flowing vapor and provided that the temperature of the first stage and any further stages is sufficiently high to keep solid from forming in the reaction apparatus.

Additional diamine is fed as either a vapor or a diamine rich liquid into reactor 32 at one or more stages lower than the top stage of the reactor to form a polymer salt stream. If fed as a liquid, the diamine undergoes substantial vaporization when it comes in contact with the hot polymerizing reaction mixture. Pre-vaporization of the diamine feed system removes some of the heat requirement from the reactor and reduces the likelihood of time to time variation in the amount of diamine vapor flow at various points in the reactor.

Near-infrared analysis can be used at almost any time after the addition of the diamine. Based on the NIR analysis, changes can be made in the diamine feed into or near the bottom stage of the reactor system. By "into or near" is meant that the diamine is fed into the bottom reactor stage, into the stage immediately above the bottom stage or into transfer line 18 leading out of the bottom reactor stage. Most preferably, this feed is into transfer line 18. Balanced product from transfer line 18 is generically described, in the case of nylon 6,6 processing, as intermediate molecular weight nylon. As such it is suitable for sale as is, or it can be further processed through spinning machine 20 to yarn or to high molecular weight nylon by methods known in the art, for example in an extruder or through solid phase polymerization.

As shown in FIG. 1B, representative in-line near-infrared spectroscopic (NIR) probes 24 are placed between mixer 30 and reactor 32 and between reactor 32 and pelletizer 22. Representative at-line probes are shown in FIG. 1B, after pelletizer 22 and after spinning machine 20. The absorbance of the polymer feed stream measured in-line at at least one selected point along the process route can be continuously determined by NIR probe 24. The probe outputs a process signal to NIR analyzer 26. The analyzer computer processes the process signal and generates an output signal, representative of the predicted value of the characteristic of interest. The output signal is compared to the preselected desired characteristic value and appropriate control action is taken by adjusting a process variable.

A specific application of the present invention is at the melt phase stage where near-infrared measurements can be used to measure and control product from the polyamide polymerization process. In a preferred mode, where nylon 6,6 is being prepared in polymerizer 16 of FIG. 1A or reactor 32 of FIG. 1B, NIR can be used to measure and control the ends balance, i.e., the balance of amine ends and carboxylic acid ends, and the degree of conversion of the polyamidation reaction, which is related to relative viscosity. The ends balance and the conversion are specified by determining any two of the following: amine ends concentration ($[A]$), carboxyl ends concentration ($[C]$), difference of ends (DE or $[C]-[A]$) and sum of ends (SE or $[C]+[A]$). Polymer RV can be used in place of sum of ends. The analysis and control can be carried out essentially continuously. In a preferred process for the manufacture of nylon 6,6, based on the number of carboxylic acid ends and amine ends or on the difference in ends, a variable amount of hexamethylenediamine can be injected near the bottom stage of reactor 32, as shown in FIG. 1B, in order to bring the measured characteristic, for example, ends, ends balance and/or RV, closer to the preselected desired value for that characteristic. Other process control actions comprise adjustment to residence time, temperature and pressure.

A further application of near-infrared process control is in the manufacture of spandex, which is a manufactured filament or fiber in which the fiber-forming substance is a long chain synthetic polymer composed of at least 85% by weight of a segmented polyurethane. The polyurethane is ordinarily prepared by reacting a polyester diol, a polyether diol, or a polycarbonate diol with a diisocyanate such as methylene-bis(4-phenylisocyanate) to form a capped glycol, which is then chain-extended in a solvent with diamines such as 1,2-diaminoethane, 2-methyl-1,5-pentanediamine, 1,3-cyclohexanediamine, and the like. The polymer is then dry-spun into filaments. At appropriate points in the process, monitoring the near-infrared spectrum in the 1000 to 2000 nm region can aid in process control. Isocyanate ends are detected between 1000 and 1300 nm and between 1600 and 1700 nm; the results can be used to adjust the ratio of polymeric diol to diisocyanate. Amine ends are detected between 1400 and 1600 nm; the results can be used to correct the amount of aliamines added as chain extenders. The region between 1100 and 1300 nm can be used to detect percent solids in the solution, which is adjusted by varying the amount of solvent added. When the solvent is recovered, trace amounts of water are detected in the region between 1900 and 2000 nm, and the temperature in the dehydration column can be adjusted to bring the water content to an acceptable level.

A further embodiment of the present invention is the use of NIR to analyze polyamides in the solid state. These analyses can be used in the control of manufacturing processes or on "final" samples to verify the quality of what has been produced. The polyamide is preferably in the form of flakes, pellets or fibers. NIR measurement can be performed at-line for solid phase polyamide, for example, after spinning, as shown in FIGS. 1A and 1B.

Additives can be introduced during the process to impart certain desirable properties to the final product. Control of specific application additives such as $TiO_2$ or other pigments can be done in the melt or solid phase.

Figure 2:
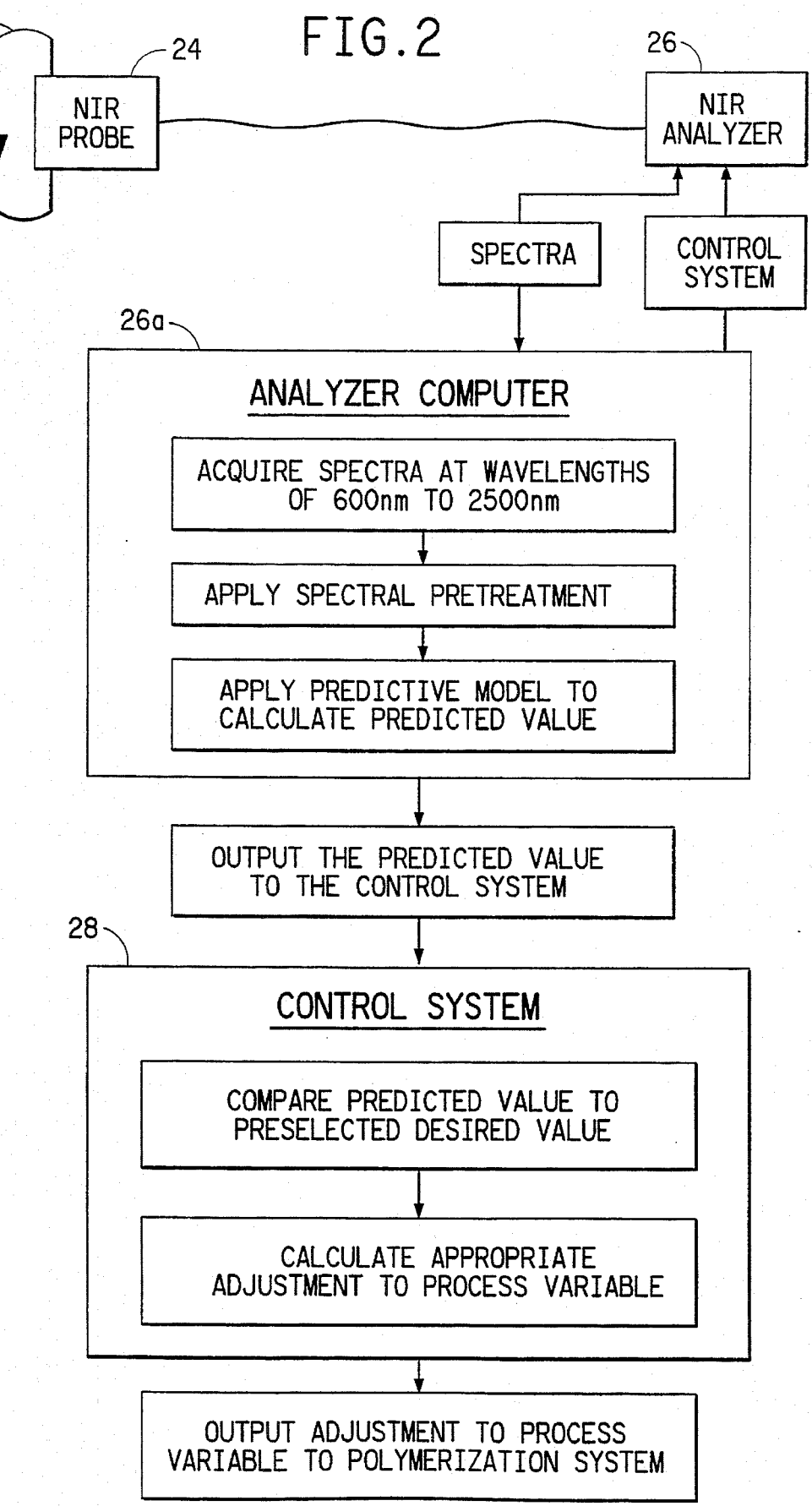
FIG. 2 is a flowsheet of steps performed in a near-infrared analyzer and in a control system.

Referring now to FIG. 2, NIR analyzer 26 obtains a process signal from NIR probe 24 located in-line or at-line, and sends spectra to NIR analyzer computer 26a. The computer performs two functions (1) sending control commands to the NIR analyzer, and (2) performing calculations on the spectra to determine a predicted value of at least one characteristic of interest. The calculations utilize spectra acquired for wavelengths within the range of about 600 nm to about 2500 nm, on which the computer first applies spectral pretreatment, for example, smoothing, derivatization, mean centering and/or baseline correction, for the various wavelengths to generate a pretreated spectrum. The computer then applies a predictive model in the form of an equation to the intensity of the pretreated spectrum for the absorbance region representative of at least part of the chemical species which are undergoing change during the reaction in the polyamide precursor mixture or in the resultant polyamide or copolyamide to generate a predicted value for the characteristic of interest. The NIR computer outputs the predicted value to a control system, usually a computer, which then takes appropriate action depending on a programmed control algorithm based on a comparison of the predicted value to a preselected desired value for the characteristic.

Near-infrared (NIR) spectroscopy is conducted with specialized equipment known as the near-infrared (NIR) spectrometer. There are several suppliers of such equipment, including UOP/Guided Wave, El Dorado Hills, Calif.; NIRSystems, Silver Spring, Md.; Perkin Elmer, Norwalk, Conn., Varian Associates, Sunnyvale, Calif., Moisture Systems Corp., Hopkinton, Mass. and LT Industries, Inc. Rockville, Md. The equipment vendors normally supply, with their equipment, a comprehensive set of operating software, which permits the user to operate his or her NIR spectrometer and to analyze the data. A computer is attached to the spectrophotometer for control of the device and interpretation Of the spectral data.

Dedicated near-infrared spectrometers or modified laboratory NIR spectrometers of conventional design can be used with the invention. Preferred modes of operation are transmission, reflectance, and transflectance. Suitable spectrometers are the NIRSystems model 6500; LT Industries Model 1200; and the UOP/Guided Wave model 300 series. The spectrometer can be operated on a batch basis (receiving signals, e.g., by a sample feeding arrangement), or more preferably, on a continuous basis in which the fluid to be measured flows through a cell, or a probe is immersed in the flowing fluid, and light is transmitted through a fiber-optic cable to and from the spectrophotometer.

When a spectrophotometer is used to scan a process stream, a lengthy series of discrete results are collected at each wavelength step by the instrument. The resulting response at each wavelength is expressed in transmittance (T), reflectance (R), or absorbance (A) units, A being equal to log (1/T). When T=1, no absorbance occurs; while when T=0, infinite absorbance occurs. The absorbance may be measured as the absorbance or as the first, second, third, fourth or higher derivative of absorbance or by other signal processing techniques. Generally, multiple scans are made (two or more) and stored. When these results are plotted vs. wavelength, a spectrum (curve) is produced. Appropriate mathematical pretreatment can be applied to the spectrum which is then stored together with analytical data in order to prepare a calibration set of known data for regression analysis. The calibration set is then subjected to various regression analysis methodologies in order to create a predictive model in the form of a mathematical expression for calculating the characteristic measurement of interest from the spectral responses.

In general, the predictive model is created by establishing by independent means the value of each characteristic of interest for each of a statistically meaningful number of samples, divided into a calibration set and a validation set. Multiple scans are made of each sample of the calibration set with a near-infrared spectrometer operatively connected to a computer programmed to perform statistical analysis of data, to obtain by coaddition the spectral response of each sample—its transmittance, reflectance, or absorbance—at each wavelength within the range of about 600 nm to about 2500 nm. A data matrix is then statistically generated for the totality of the samples of the calibration set correlating their spectral response at each wavelength to the value of the characteristic previously established by independent means. From this data matrix a mathematical expression in the form of a predictive equation is formulated for calculating the measured value of the characteristic of interest. The accuracy of the predictive equation can be established by applying the equation to calculate the predicted characteristic value of the samples in the calibration set. If the predicted value of the samples of the calibration set are not within a predetermined degree of error from the previously established value, then the predictive equation is modified in a statistically acceptable manner until the resulting predictive equation predicts the value of the calibration set within a predetermined degree of error. The same conditions are used for measuring the spectral responses of the validation set and applying the predictive equation obtained from the calibration set to produce the value for each sample of the validation set. The predictive value of each sample of the validation set is then compared with the value established by independent means. If the results indicate that the predictive equation does not predict the value of the validation set within a predetermined degree of error, then the predictive equation is further modified in a statistically acceptable manner until it predicts the value of the validation set at least to that degree.

The predictive mathematical model created during the calibration process described above is then routinely applied to the measurement of the same species in the process stream or resultant polyamide, preferably in-line. The routine analyses are undertaken at process conditions which are within the envelope of conditions used during the calibration process. The routine spectra are subjected to the identical data treatments utilized with the calibration set spectra.

There are many well-known mathematical techniques of correlation of NIR spectral responses. They include, for example, "Single-Term Linear Regression," "Multiterm Linear Regression," "Component Spectrum Reconstruction," and "Discriminant Analysis" methods explained in an article by W. R. Hruschka at pp. 35–55 of Near Infrared Technology in the Agricultural and Food Industries, P. C. Williams et at., Editors, American Association of Cereal Chemists, Inc. St. Paul, Minn. 1987 ("Williams"). Other techniques include, for example "Hruschka Regression," "Fourier Transform Regression," "Principal Component Regression," and "Partial Least Squares Regression" methods explained in detail in an article by H. Martens et al., at pp. 57–87 of Williams. In Chapter 3 of Multivariate Calibration, H. Martens et at., John Wiley & Sons, Ltd., Chichester, U.K. 1989, more techniques, including, for example, "Univariate Calibration," "Bilinear Modeling," "Self Deconvolution," "Target Transformation Factor Analysis," "Rank Annihilation Method," "Step-wise Multiple Linear Regression," "Ridge Regression," "Nonlinear Regression," and "Nonparametric Regression" are taught. The "Neural Network" technique explained in D. E. Rumelhart et at. in Parallel Distributed Processing-Explorations in the Microconstruction of Cognition, Vol. 1, Foundations 1986; Vol. 2, Psychological and Biological Models, 1986; and Vol. 3, A Handbook of Models, Programs and Exercises, 1988, MIT Press Cambridge, Mass., may also be applied.

Some commercially available software packages include, for example, "Near-Infrared Spectral Analysis Software" (NSAS) by NIRSystems, Inc., Silver Spring, Md.; "Unscrambler" by Camo A/S, Trondheim, Norway; "Spectra Metrix," "LightCal," and "LightCal Plus" by LT Industries Corporation, Rockville, Md.; and "InfraAnalyzer Data Analysis System" (IDAS) and "Principal Component Analysis Program" (PCA-pc) by Bran+Luebbe Analyzing Technologies, Inc.

The results of measurement determinations can be transmitted instantaneously to a process control system, whose role is to control the process variables such as, the temperature and the pressure of the polymerization, and the feed of the various reactants to the polymerization reactor so that the characteristic of the polyamide or copolyamide manufactured can be continually very close to the preselected desired value. One embodiment of control is an automated distributive control system (DCS) comprising a process computer which is advantageously linked directly to the near-infrared analyzer. The process control computer is provided with an algorithm by which it controls the process variables by way of links to, for example, the polymerizer or reactor. Another embodiment of control comprises simple monitoring by an operator who makes appropriate manual adjustments to process variables.

EXAMPLE 1

In order to calibrate the spectrometer, near-infrared spectra of nylon 6,6 salt samples were obtained using a NIRSystems Model OL5500 near-infrared spectrometer equipped with a 5 foot fiber-optic bundle and an interactance probe (NIRSystems, Silver Springs, Md.). The interactance probe was inserted directly into a Pyrex round-bottom flask containing the salt samples, through a standard 24/40 fitting. The optical pathlength was 2.5 inches.

The salt samples were made up by weight to span the range in composition from 49.0 to 51.6% salt and −200 to +200 difference of ends (approximately 6.4 to 9.0 pH). Three absorbance spectra (each the average of 32 scans) were acquired and saved for each salt sample at each of three temperatures in the range 37° to 43° C. The composition of each sample was calculated from the weights of ingredients used and reported to the nearest 0.1 end (0.002 pH units) and 0.01% salt. The result was a calibration set containing 303 spectra.

Both multilinear regression (MLR) and partial least squares (PLS) models were developed using NIRSystems' NSAS chemometrics software package following the directions supplied by the vendor. A three-factor PLS model based on second derivative spectra in the wavelength range 700 nm to 1100 nm, considering only the samples in the range from −200 to +25 ends (7.1 to 9.0 pH), predicted the ends difference with an accuracy (standard error of performance) of 2.5 ends (0.06 pH units) and a correlation coefficient (R) of 0.9994. A four-factor PLS model based on absorbance spectra in the wavelength range 800–1100 nm, considering all samples, predicted salt concentration with an accuracy (SEC) of 0.05% and a correlation coefficient (R) of 0.9981.

Validation was done by predicting composition data with these models continuously on-line, in a continuous nylon 6,6 salt strike unit. The NIR probe was inserted directly into the aqueous salt stream using a cell located on a recirculation instrument loop. The optical pathlength was 2.5 inches. The best prediction precision was about 0.3–0.6 ends (0.007 to 0.014 pH units) and about 0.01% salt.

EXAMPLE 2

In order to calibrate the spectrometer, near-infrared spectra of nylon 6,6 salt samples were obtained using a NIRSystems Model OL5500 near-infrared spectrometer. A pair of 5.74"×1" diameter sapphire-windowed optical transmission probes (NIRSystems) were inserted directly into the aqueous salt stream using a cell located on a recirculation instrument loop. The NIR cell is designed to allow an optical pathlength from 4" to 6". The transmission probes were connected to the spectrometer with 5 foot fiber-optic bundles.

Calibration was done off-line, using a heated cell of the desired pathlength, and on-line. Off-line, a series of salt samples were made up by weight to span a wider range of compositions than usually encountered on-line. Calibration models were developed on samples for 7.42 to 8.14 pH and 50.3% to 51.5% salt at temperatures ranging from 39.1° to 41.4° C.

Calibrations were made using spectra obtained on-line. The near-infrared monitoring system was programmed to automatically scan and save an absorbance spectrum (the average of 32 scans) of the aqueous salt every five minutes. Periodically, discrete samples were taken from the recirculating loop and analyzed in the laboratory for pH. (The pH of interest is that of an approximately 9.5% weight percent salt solution.). The NIR spectra nearest in time to each of the discrete samples collected were extracted from the spectra in a data set covering a period of three months to give a calibration set of 33 samples. The calibration set spanned a pH range of 7.72 to 8.01.

Partial least squares (PLS) models were developed using NIRSystems' NSAS chemometrics software package following the directions supplied by the vendor. A four-factor PLS model based on second derivative spectra in the wavelength range of 1020 nm to 1080 nm predicted the pH with an accuracy (SEC) of 0.04 pH units and a correlation coefficient (R) of 0.8605. Validation was done by predicting pH with this model during the same operations. The standard error of performance (SEP) was 0.039 pH units and the correlation coefficient (R) was 0.775. Further validation was done by predicting pH in real time with this model during additional operations. The predictions tracked the pH results obtained manually and responded correctly to process changes made.

EXAMPLE 3

In a demonstration of the preferred process, the preparation of nylon 6,6 from an acid-rich feed, near-infrared spectra of the acid-rich feed were obtained using a UOP/Guided Wave Model 300P near-infrared spectrometer (UOP/Guided Wave, El Dorado, Calif.). A pair of 5.5"×0.25" diameter sapphire-windowed optical transmission probes (UOP/Guided Wave) were inserted directly into the 0.25" tubing exit stream of the acid-rich feed unit using a Swagelok® cross, available from Swagelok Co., Solon, Ohio, and two Conax® fittings equipped with Viton® o-ring seals, both available from Conax Buffalo Corp., Buffalo, N.Y. The optical pathlength between the probes was about 5 mm. The probes were connected to the spectrometer using 20 meters of jacketed 500 micron single fiber optic cable (UOP/Guided Wave).

During a two day test run, the acid-rich feed composition was varied stepwise from 77% adipic acid to 85% adipic acid. The near-infrared monitoring system was programmed to automatically scan and save an absorbance spectrum (the average of 8 scans) of the acid-rich feed once every five minutes. At roughly half-hour intervals, discrete samples were taken at the exit of the acid-rich feed unit (a few inches beyond the NIR probes). The samples were analyzed by titration. 25 g of acid-rich feed was dissolved in 325 mL of water at 25° C. The solution was titrated with a 50% by weight solution of hexamethylene diamine in water to a potentiometric endpoint of 7.600 pH. The calculations assumed a sample moisture level of 2.0% and no conversion of diacid and diamine to nylon 6,6 polymer. The lab results were reported as weight percent adipic acid (dry basis) to the nearest 0.1 percent.

At the conclusion of the test, the NIR spectra nearest (within 5 minutes) in time to each of the lab samples were extracted from the spectra in the data set to give a calibration set of 57 spectra. The calibration spectra were smoothed and baseline corrected using the Scanner 300 software supplied with the UOP/Guided Wave spectrometer.

Partial least squares (PLS) models were developed using the wavelength region between 1000 nm and 1670 nm. The PLS models were developed using the Unscrambler® (Camo A/S, Trondheim, Norway) chemometric software package following the directions supplied by the vendor. A two-factor PLS model explained 99.6% of the X-variance and 97.3% of the Y-variance in the calibration set. It predicted the acid-rich feed composition with an accuracy (standard error of performance) of 0.17% adipic acid and a correlation coefficient (R) of 0.989.

Validation was done by predicting composition data with this model for the other obtained spectra. The model predictions tracked the lab results, responded correctly to known process changes, and had a repeatability (standard deviation of consecutive predictions) of 0.03% adipic acid.

Further validation was done by predicting composition data with this model (in real time) during a subsequent test run. During this run the model predictions tracked the lab results (although with an offset of about −0.6% adipic acid), responded correctly to known process changes, and had a repeatability of 0.02% adipic acid.

This model was used to control the composition of the acid-rich feed in a subsequent experiment. Depending on the value of % adipic acid measured, and its comparison with a desired value, changes in the reactant ratios were made.

EXAMPLE 4

In monitoring the exit stream of polymer melt from the reactor, the goal is to first measure then control the ends balance and the conversion. In the case of the preferred embodiment, the preparation of nylon 6,6, the ends balance and the conversion are specified by determining any two of the following: amine ends concentration ([A]), carboxyl ends concentration ([C]), difference of ends (DE or [C]−[A]) and sum of ends (SE or [C]+[A]). Polymer relative viscosity (RV) can be used in place of sum of ends. The analysis and control may be carried out essentially continuously.

In the preparation of nylon 6,6, near-infrared spectra of the polymer melt were obtained using a UOP/Guided Wave Model 300P near-infrared spectrometer. A pair of 5.5"×0.25" diameter sapphire-windowed optical transmission probes (available from UOP/Guided Wave, El Dorado Hills, Calif.) were inserted directly into the exit stream of the reactor using a NIR cell located at the exit of the reactor. The NIR cell consisted of a block of 316 stainless steel through which perpendicular holes had been drilled; the polymer melt flowed through a 5 mm diameter channel the length of the cell; the Guided Wave probes were inserted perpendicular to the flow and held in place with Conax® fittings (Conax Buffalo Corp., Buffalo, N.Y.) and Kalrez® seals (E. I. du Pont de Nemours and Company, Wilmington, Del.). The optical pathlength between the probes was about 5 mm. Two flat band-heaters were placed around the block cell. The probes were connected to the spectrometer using 20 meters of jacketed 500 micron single fiber optic cable (UOP/Guided Wave).

During a three day test run, the near-infrared monitoring system was programmed to automatically scan and save an absorbance spectrum (the average of 8 scans) of the polymer melt once every five minutes. At roughly fifteen minute intervals, discrete samples were taken at the exit of the reactor (a few inches beyond the NIR cell). The samples were analyzed by titration to determine the acid and amine end concentrations, [C] and [A]. See Volume 17 of the "Encyclopedia of Industrial Chemical Analysis" published by John Wiley and Sons (1973), page 293. The lab results were reported as acid and amine ends, in meq ends/kg polymer, to the nearest 0.1 end.

At the conclusion of the test, the NIR spectra nearest (within 5 minutes) in time to each of the lab samples collected were extracted from the spectra in the data set to give a calibration set of 26 samples. The calibration set spanned a range of 100 to 400 amine ends and 50 to 170 acid ends. The calibration spectra were smoothed and baseline corrected using the Scanner 300 software supplied with the UOP/Guided Wave spectrometer.

Partial least squares (PLS) models were developed using the wavelength region between 1000 and 2100 nm. PLS models were developed using the Unscrambler® (Camo A/S, Trondheim, Norway) chemometrics software package following the directions supplied by the vendor. For amine ends, a two-factor PLS model explained 98.0% of the X-variance and 97.2% of the Y-variance in the calibration set. It predicted the polymer composition with an accuracy (standard error of performance) of 15.8 amine ends and a correlation coefficient (R) of 0.987.

This calibration set did not contain sufficient variation to independently model acid ends.

Validation was done by predicting composition data with this model in real time during subsequent unit operations. The model predictions were converted using an empirical linear equation from amine ends ([A]) to difference of ends (DE) for operator convenience, since it was found that over the short term, the amine ends values and the difference of ends values are highly correlated. The resulting DE predictions tracked the lab results (although with an offset that changed periodically), responded correctly to known process changes, and had repeatability (standard deviation of consecutive predictions) of 1.3 ends over an hour and 0.95 ends over a ten minute period.

This model was used to control the composition of the polymer melt in a subsequent test. Depending on the value of DE obtained and its comparison to the desired value, changes in the reactor operation were made.

EXAMPLE 5

In monitoring the exit stream of polymer melt from the reactor, the goal is to first measure then control the ends balance and the conversion. In the case of the preferred embodiment, the preparation of nylon 6,6, the ends balance and conversion are both specified by determining any two of the following: amine ends concentration ([A]), carboxyl ends concentration ([C]), difference of ends (DE or [C]–[A]) and sum of ends (SE or [C]+[A]). The analysis and control can be carried out essentially continuously.

In the preparation of nylon 6,6, near-infrared spectra of the polymer melt were obtained using a UOP/Guided Wave Model 300P near-infrared spectrometer. A pair of 5.5"×0.25" diameter sapphire-windowed optical transmission probes (UOP/Guided Wave) were inserted into sapphire-windowed stainless steel "sleeves" in a NIR cell located in the transfer line following the reactor. The probes did not directly contact the polymer melt. The cell was heated by hot oil. The optical pathlength between the probes was 5 mm. The probes were connected to the spectrometer using about 100 meters of jacketed 500 micron single fiber optic cable (UOP/Guided Wave).

The near-infrared monitoring system was programmed to automatically scan and save an absorbance spectrum (the average of 8 scans) of the polymer melt once every fifteen minutes. Once an hour discrete samples were taken at the pelletizer at the end of the transfer line. The samples were analyzed by titration to determine the difference of ends, DE, and the amine end concentration, [A]. See Volume 17 of the "Encyclopedia of Industrial Chemical Analysis" published by John Wiley and Sons (1973), page 293. The lab results were reported in meq ends/kg polymer or "ends" to the nearest 0.1 end.

Over a four day period, the NIR spectra nearest (within 5 minutes) in time to each of the lab samples collected were extracted from the spectra in the data set to give a calibration set of 67 samples. The calibration set spanned a range of −167.0 to +81.0 difference of ends and 33.0 to 221.4 amine ends. The calibration spectra were smoothed and baseline corrected using the Scanner 300 software supplied with the UOP/Guided Wave spectrometer.

Partial least squares (PLS) models were developed using the wavelength region between 1504 nm and 1576 nm. The PLS model was developed using the Unscrambler® (Camo A/S, Trondheim, Norway) chemometrics software package following the direction supplied by the vendor. For difference of ends, a two-factor PLS model explained 99.1% of the X-variance and 95.2% of the Y-variance in the calibration set. It predicted the polymer composition with an accuracy (standard error of performance) of 13.3 ends and a correlation coefficient (R) of 0.977. This calibration set did not contain sufficient variation to independently model sum of ends.

Validation was done by predicting composition data with this model for a different two day period. The model predictions tracked the lab results (though with an offset that changed periodically) and had a repeatability (standard deviation of consecutive predictions) of 1.5 ends over an hour and 0.50 ends over a ten minute period.

A model obtained in a similar manner was used to control the composition of polymer melt in a subsequent test run. Depending on the value of DE measured and its comparison with a desired value, changes in the reactor operation were made.

What is claimed is:

1. A method for measuring and controlling at least one characteristic of a dimonomeric polyamide, copolyamide, or polyamide precursor mixture in a polymerization process stream, comprising the steps of:
   (a) creating a predictive model for the value of the characteristic;
   (b) acquiring spectra by measuring the near-infrared absorbance of the polyamide, copolyamide or polyamide precursor mixture in-line at least one selected point in the polymerization process stream at wavelengths within the near-infrared range;
   (c) applying spectral pretreatment to the measurements of step (b) to obtain a pretreated spectrum;
   (d) applying the predictive model to the spectrum to calculate a predicted value of the characteristic;
   (e) comparing the predicted value of the characteristic to a preselected desired value of the characteristic; and
   (f) controlling the characteristic by making an adjustment to at least one process variable of the polymerization process stream.

2. The method of claim 1 wherein the polyamide is nylon 6,6.

3. The method of claim 1 wherein the polyamide precursor mixture comprises adipic acid and hexamethylenediamine for the preparation of nylon 6,6.

4. The method of claim 1 wherein the characteristic is selected from the group consisting of:
   concentration of carboxylic acid ends, concentration of amine ends, ends balance, relative viscosity, dyeability, concentration of finish on yarn, and additive concentration.

5. The method of claim 1 wherein the process variable to be adjusted is selected from the group consisting of: flow rate of diacid; flow rate of diamine; flow rate of additive; residence time; temperature; and pressure.

6. The method of claim 3 wherein the polyamide precursor mixture is an aqueous salt solution and the near-infrared absorbance is measured at wavelengths within the range of about 700 nm to about 1100 nm.

7. The method of claim 3 wherein the polyamide precursor mixture is a non-aqueous acid-rich feed and the near-infrared absorbance is measured at wavelengths within the range of about 1000 nm to about 1670 nm.

8. The method of claim 3 wherein the polyamide precursor mixture is a polymer melt and the near-infrared absorbance is measured at wavelengths within the range of about 1000 nm to about 2100 nm.

9. The method of claim 7 wherein step (f) comprises adding diamine into or near the bottom stage of a reactor used in the polymerization process.

10. A method for measuring at least one characteristic of a solid phase dimonomeric polyamide or copolyamide and controlling said characteristic in a polymerization process stream, comprising the steps of:
    (a) creating a predictive model for the value of the characteristic;
    (b) acquiring spectra by measuring the near-infrared absorbance of the polyamide or copolyamide at-line within the near-infrared range;

(c) applying spectral pretreatment to the measurements of step (b) to obtain a pretreated spectrum;

(d) applying the predictive model to the spectrum to calculate a predicted value of the characteristic;

(e) comparing the predicted value of the characteristic to a preselected desired value of the characteristic; and (f) controlling the characteristic by making an adjustment to at least one process variable of the polymerization process stream.

11. The method of claim 10 wherein the polyamide is nylon 6,6.

12. The method of claim 10 wherein the characteristic is selected from the group consisting of:

concentration of carboxylic acid ends, concentration of amine ends, ends balance, relative viscosity, dyeability, concentration of finish on yarn, and additive concentration.

13. The method of claim 10 wherein the process variable to be adjusted is selected from the group consisting of: flow rate of diacid; flow rate of diamine; flow rate of additive; residence time; temperature; and pressure.

* * * * *